US011024417B2

(12) United States Patent
Kohle et al.

(10) Patent No.: US 11,024,417 B2
(45) Date of Patent: Jun. 1, 2021

(54) INTEGRATED MEDICAL IMAGE VISUALIZATION AND EXPLORATION

(71) Applicants: Siemens Healthcare GmbH, Erlangen (DE); FRAUNHOFER-GESELLSCHAFT ZUR FÖRDERUNG DER ANGEWANDTEN FORSCHUNG E.V., Munich (DE)

(72) Inventors: Sven Kohle, Erlangen (DE); Christian Tietjen, Fuerth (DE); Marcus Thaele, Fuerth (DE); Steffen Weichert, Hannover (DE); Johannes Baeck, Hannover (DE); Felix Nensa, Essen (DE); Mathias Neugebauer, Bremen (DE); Felix Ritter, Bremen (DE); Silvie Grossmann, Erlangen (DE)

(73) Assignees: SIEMENS HEALTHCARE GMBH, Erlangen (DE); FRAUNHOFER-GESELLSCHAFT ZUR FOERDERUNG-DER-ANGEWANDTEN FORSCHUNUG E.V., Munich (DE)

( * ) Notice: Subject to any disclaimer, the term of this patent is extended or adjusted under 35 U.S.C. 154(b) by 15 days.

(21) Appl. No.: 16/691,008

(22) Filed: Nov. 21, 2019

(65) Prior Publication Data
US 2020/0168321 A1 May 28, 2020

(30) Foreign Application Priority Data

Nov. 23, 2018 (EP) ..................................... 18208112
Sep. 23, 2019 (EP) ..................................... 19198904

(51) Int. Cl.
*G06F 3/0482* (2013.01)
*G16H 30/40* (2018.01)
(Continued)

(52) U.S. Cl.
CPC ........... *G16H 30/40* (2018.01); *G06F 3/0482* (2013.01); *G06T 7/0012* (2013.01); *G06T 11/60* (2013.01);
(Continued)

(58) Field of Classification Search
CPC ........ G16H 30/40; G16H 50/20; G16H 40/63; G06F 3/0482; G06F 2203/04804;
(Continued)

(56) References Cited

U.S. PATENT DOCUMENTS

2008/0152204 A1 6/2008 Huo et al.
2009/0073114 A1 3/2009 Bay et al.
(Continued)

FOREIGN PATENT DOCUMENTS

EP 3537454 A1 9/2019
EP 3537454 A1 9/2019
EP 3611733 A1 2/2020

OTHER PUBLICATIONS

Extended European Search Report dated Feb. 6, 2020.

*Primary Examiner* — Phuong H Nguyen
(74) *Attorney, Agent, or Firm* — Harness, Dickey & Pierce, P.L.C.

(57) ABSTRACT

A system is for supporting evaluation of a medical image data set. The system includes an interface unit to provide a display of a medical image data set, visualize an evaluation tool, visualize at least one result of an evaluation function, and receive user input relating to navigating the evaluation tool in the medical image data set to a region of interest, and selecting at least one of the evaluation functions. The system further includes a computing unit to process the user input to navigate the evaluation tool, perform the at least one evaluation function, and generate a visualization of at least one result of the evaluation function. The at least one result (Continued)

is adapted to be visualized as an overlay to the displayed image data set and/or evaluation tool.

14 Claims, 5 Drawing Sheets

(51) Int. Cl.
*G06T 7/00* (2017.01)
*G06T 11/60* (2006.01)

(52) U.S. Cl.
CPC .............. *G06F 2203/04804* (2013.01); *G06T 2200/24* (2013.01); *G06T 2207/20104* (2013.01); *G06T 2210/41* (2013.01)

(58) Field of Classification Search
CPC ... G06T 7/0012; G06T 11/60; G06T 2200/24; G06T 2207/20104; G06T 2210/41
See application file for complete search history.

(56) References Cited

U.S. PATENT DOCUMENTS

| | | |
|---|---|---|
| 2014/0143716 A1 | 5/2014 | Bergtholdt et al. |
| 2015/0213597 A1 | 7/2015 | Oh et al. |
| 2019/0279746 A1 | 9/2019 | Kohle et al. |

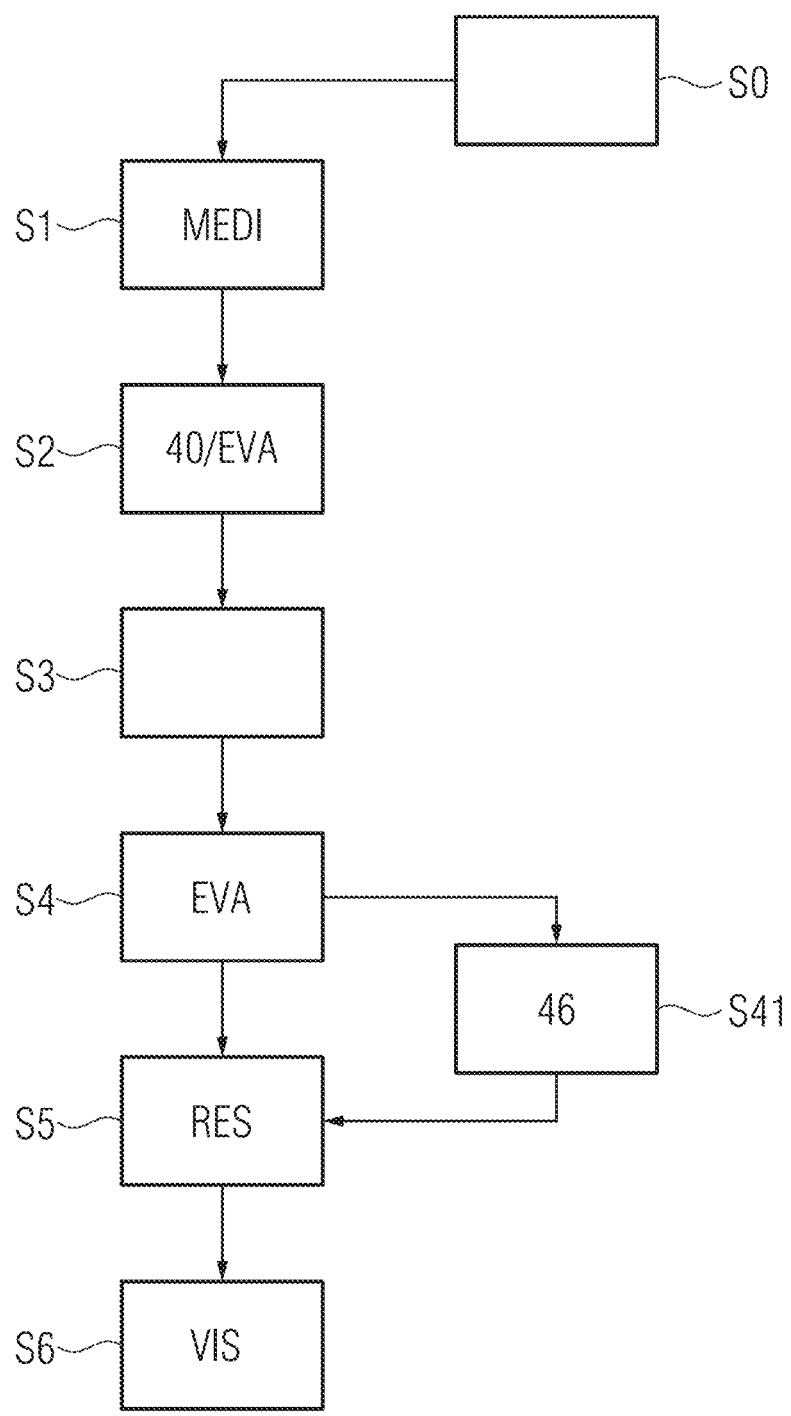

INTEGRATED MEDICAL IMAGE VISUALIZATION AND EXPLORATION

PRIORITY STATEMENT

The present application hereby claims priority under 35 U.S.C. § 119 to European patent application numbers EP 19198904.5 filed Sep. 23, 2019 and EP 18208112.5 filed Nov. 23, 2018, the entire contents of each of which are hereby fully incorporated herein by reference.

FIELD

Embodiments of the invention generally relate to a method and system for medical image visualization and exploration like visualization and exploration of computed tomography or magnetic resonance tomography images. The invention further relates to a computer program, which performs the steps of the inventive method, if the computer program is executed on a computer, and to an electronically readable storage medium, on which such a computer program is stored.

Embodiments of the present invention further relate to the former European patent applications EP 18189090 and EP 18160372 and their technical teachings, the entire contents of each of which are hereby fully incorporated herein, by reference.

BACKGROUND

Exploration of hundreds or thousands of medical images acquired by modern radiologic imaging modalities in the course of a patient's examination is ambitious and exhausting at the same time. This is because medical images need examination for different anatomical positions, but also with different imaging contrasts to identify suspicious structures or areas. Those findings further need interpretation to fully assess clinical relevance. Advances are constantly made in automated detection procedures for potentially suspicious findings as well as in automated diagnosing. However, these advances are only applicable for secondary reading, i.e. a human expert still has to finally judge clinical relevance.

One major root cause for user fatigue is the frequent switch across multiple user interfaces (UI) necessary for reviewing different sources of information (images, text, numbers). Those sources are typically distributed on different screens. Frequent eye movement, focusing on different UI elements or executing UI navigation tasks by applying mouse click interactions is the consequence. The user needs to face multiple screen areas of different brightness and contrast. Accordingly, radiologists usually work in darkened reading rooms and prefer to keep focus on reviewing and interpreting images. Any disruption ideally is to be avoided.

Studies show that significant time (>50% for many exams) users' eyes are not focusing images but on screens reviewing or writing textual information, e.g. clinical reports.

It is known to optimize the connection or integration of images and/or information/tools for specific use cases or individual preferences of a radiologist. E.g. mammography reading workstations display high resolution images on 5k monitors thereby electronically mimicking conventional magnifying glasses applied to classic lightboxes. High resolution display enables radiologists to identify and in detail inspect e.g. micro calcifications. Some oncologic applications dedicated for follow-up examination allow labeling of positions, lesions were previously reported at. Other applications provide gesture-based tool selection at the place where needed. However, improvement is only available for specific procedures or individual inspection/reporting steps.

SUMMARY

At least one embodiment of the present invention provides a computer-aided image evaluation and/or analysis tool which allows intuitive and upfront operation of a radiologic user interface. Particularly, at least one embodiment of the present invention provides devices and/or methods which avoid the need to for switching between several applications and/or screens and/or graphical interfaces.

Embodiments of the application are directed to a system for supporting evaluation of a medical image data set, a corresponding method, a corresponding computer-program product and a computer-readable medium. Alternative and/or preferred embodiments are the object of the claims.

In the following, the technical solution according to embodiments of the present invention is described with respect to the apparatuses as well as with respect to the methods. Features, advantages or alternative embodiments described herein can likewise be assigned to other objects and vice versa. In other words, claims addressing the inventive method can be improved by features described or claimed with respect to the apparatuses. In this case, e.g. functional features of the method are embodied by objective units or elements of the apparatus.

Accordingly, a first embodiment of the present invention is directed to a system for supporting evaluation of a medical image data set. The system comprises several units. The system comprises an interface unit and a computing unit.

The interface unit is configured to
  provide a display of a medical image data set to a user,
  visualize an evaluation tool wherein the evaluation tool is adapted
    to be movably arranged in the displayed image data set, and
    to provide at least two evaluation functions with respect to the displayed image data set,
  visualize at least one result of an evaluation function
  receive user input relating to
    navigating the evaluation tool in the medical image data set to a region of interest, and
  selecting at least one of the evaluation functions.

The computing unit is configured to
  process the user input to
    navigate the evaluation tool in the medical image data set to the region of interest,
    perform the at least one evaluation function, wherein performing the at least one evaluation function comprises accounting for image data within the region of interest, and
    generate a visualization of at least one result of the evaluation function.

Another embodiment of the present invention is directed to a computer-implemented method for supporting evaluation of a medical image data set. The method comprises several steps.

A first step is directed to providing a display of a medical image data set to a user. A further step is directed to visualizing an evaluation tool adapted
  to be movably arranged in the displayed image data set, and
  to provide at least two evaluation functions with respect to the displayed image data set.

A further step is directed to receiving user input relating to navigating the evaluation tool in the medical image data set to a region of interest and to selecting at least one of the evaluation functions. A further step is directed to processing the user input to navigate the evaluation tool in the medical image data set to the region of interest and perform the at least one evaluation function.

Another step is directed to generating a visualization of at least one result of the evaluation function. And a further step is directed to visualizing the result of the evaluation function.

At least one embodiment of the invention further provides a visualization of the evaluation and/or analysis tool via the display screen. The tool preferably has a predefined size and shape. However, both may be adapted according to user preferences or specific requirements of the displayed image data set based on corresponding user request or automatically. The evaluation tool may be automatically visualized as soon as an image evaluation software or application is started and/or the display of the medical image data set is requested or started by a user. However, the evaluation tool may also be deactivated, i.e. hidden and/or (re-) activated upon user request. The evaluation tool may be initially positioned in a preset default position, e.g. in one corner or the center of the displayed image data set.

Another embodiment of the present invention is directed to a computer program product comprising program elements which induce a computing unit of a system for supporting evaluation of a medical image data set, to perform the steps according to an embodiment of the inventive method, when the program elements are loaded into a memory of the computing unit.

Another embodiment of the present invention is directed to a computer-readable medium on which program elements are stored that are readable and executable by a computing unit of a system for supporting evaluation of a medical image data set, in order to perform steps of an embodiment of the inventive method, when the program elements are executed by the computing unit.

At least one embodiment of the present invention is directed to a system for supporting evaluation of a medical image data set, the system comprising an interface unit configured to provide a display of a medical image data set to a user, visualize an evaluation tool, the evaluation tool being adapted to be movably arranged in the medical image data set displayed, and to provide at least two evaluation functions with respect to the medical image data set displayed, visualize at least one result of an evaluation function receive user input relating to navigating the evaluation tool in the medical image data set to a region of interest, and selecting at least one evaluation function of the at least two evaluation functions, and a computing unit configured to process the user input to navigate the evaluation tool in the medical image data set to the region of interest, perform the at least one evaluation function selected, performing of the at least one evaluation function selected including accounting for image data within the region of interest, and generate a visualization of at least one result of the evaluation function, wherein the at least one result is adapted to be visualized as an overlay to at least one of the medical image data set displayed and an evaluation tool.

At least one embodiment of the present invention is directed to a computer-implemented method for supporting evaluation of a medical image data set, the method comprising:

providing a display of a medical image data set to a user, visualizing an evaluation tool adapted to be movably arranged in the medical image data set displayed, and to provide at least two evaluation functions with respect to the medical image data set displayed, receiving user input relating to navigating the evaluation tool in the medical image data set to a region of interest and relating to selecting at least one of the at least two evaluation functions, processing the user input to navigate the evaluation tool in the medical image data set to the region of interest, and perform the at least one evaluation function selected, wherein performing of the at least one evaluation function selected includes accounting for image data within the region of interest, generating a visualization of at least one result of the at least one evaluation function selected, and visualizing the at least one result of the at least one evaluation function selected, wherein the at least one result is visualized as at least one of an overlay to the medical image data set displayed and an evaluation tool.

At least one embodiment of the present invention is directed to a non-transitory computer program product storing program elements to induce a computing unit of a system, for supporting evaluation of a medical image data set, to perform the method of an embodiment, when the program elements are loaded into a memory of the computing unit and executed by the computing unit.

At least one embodiment of the present invention is directed to a non-transitory computer-readable medium storing program elements, readable and executable by a computing unit of a system for supporting evaluation of a medical image data set, to perform the method of an embodiment, when the program elements are executed by the computing unit.

BRIEF DESCRIPTION OF THE DRAWINGS

Characteristics, features and advantages of the above described invention, as well as the manner they are achieved, become clearer and more understandable in the light of the following description and embodiments, which will be described in detail with respect to the figures. This following description does not limit the invention on the contained embodiments. Same components or parts can be labeled with the same reference signs in different figures. In general, the figures are not to scale. In the following:

FIG. 5 depicts an inventive method for supporting evaluation of a three-dimensional medical image data set according to an embodiment of the present invention.

DETAILED DESCRIPTION OF THE EXAMPLE EMBODIMENTS

Figure 1:
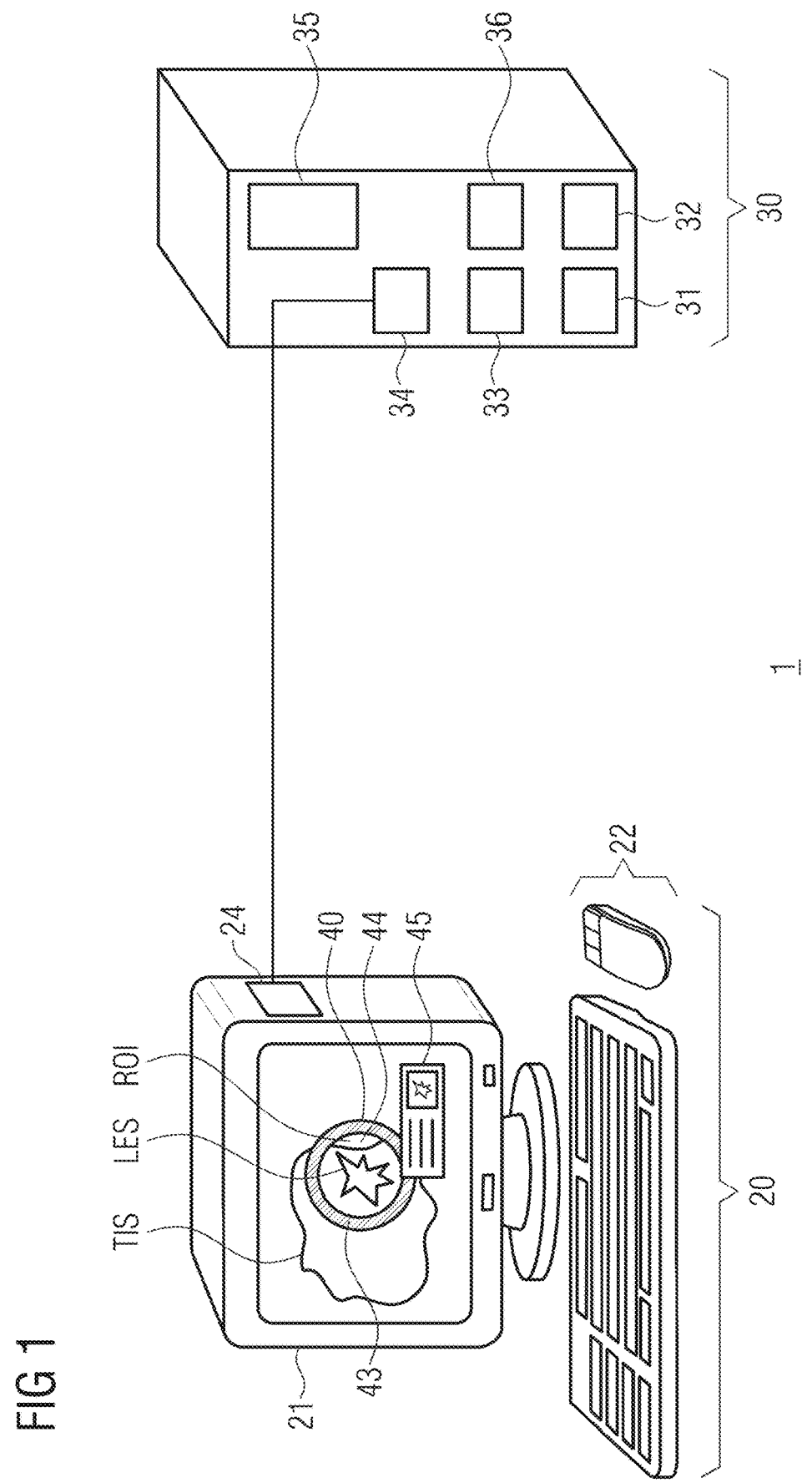
FIG. 1 depicts an inventive system for performing at least one medical imaging procedure according to an embodiment of the present invention.

The drawings are to be regarded as being schematic representations and elements illustrated in the drawings are not necessarily shown to scale. Rather, the various elements are represented such that their function and general purpose become apparent to a person skilled in the art. Any connection or coupling between functional blocks, devices, components, or other physical or functional units shown in the drawings or described herein may also be implemented by an indirect connection or coupling. A coupling between components may also be established over a wireless connection. Functional blocks may be implemented in hardware, firmware, software, or a combination thereof.

Various example embodiments will now be described more fully with reference to the accompanying drawings in which only some example embodiments are shown. Specific structural and functional details disclosed herein are merely representative for purposes of describing example embodiments. Example embodiments, however, may be embodied in various different forms, and should not be construed as being limited to only the illustrated embodiments. Rather, the illustrated embodiments are provided as examples so that this disclosure will be thorough and complete, and will fully convey the concepts of this disclosure to those skilled in the art. Accordingly, known processes, elements, and techniques, may not be described with respect to some example embodiments. Unless otherwise noted, like reference characters denote like elements throughout the attached drawings and written description, and thus descriptions will not be repeated. The present invention, however, may be embodied in many alternate forms and should not be construed as limited to only the example embodiments set forth herein.

It will be understood that, although the terms first, second, etc. may be used herein to describe various elements, components, regions, layers, and/or sections, these elements, components, regions, layers, and/or sections, should not be limited by these terms. These terms are only used to distinguish one element from another. For example, a first element could be termed a second element, and, similarly, a second element could be termed a first element, without departing from the scope of example embodiments of the present invention. As used herein, the term "and/or," includes any and all combinations of one or more of the associated listed items. The phrase "at least one of" has the same meaning as "and/or".

Spatially relative terms, such as "beneath," "below," "lower," "under," "above," "upper," and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below," "beneath," or "under," other elements or features would then be oriented "above" the other elements or features. Thus, the example terms "below" and "under" may encompass both an orientation of above and below. The device may be otherwise oriented (rotated 90 degrees or at other orientations) and the spatially relative descriptors used herein interpreted accordingly. In addition, when an element is referred to as being "between" two elements, the element may be the only element between the two elements, or one or more other intervening elements may be present.

Spatial and functional relationships between elements (for example, between modules) are described using various terms, including "connected," "engaged," "interfaced," and "coupled." Unless explicitly described as being "direct," when a relationship between first and second elements is described in the above disclosure, that relationship encompasses a direct relationship where no other intervening elements are present between the first and second elements, and also an indirect relationship where one or more intervening elements are present (either spatially or functionally) between the first and second elements. In contrast, when an element is referred to as being "directly" connected, engaged, interfaced, or coupled to another element, there are no intervening elements present. Other words used to describe the relationship between elements should be interpreted in a like fashion (e.g., "between," versus "directly between," "adjacent," versus "directly adjacent," etc.).

The terminology used herein is for the purpose of describing particular embodiments only and is not intended to be limiting of example embodiments of the invention. As used herein, the singular forms "a," "an," and "the," are intended to include the plural forms as well, unless the context clearly indicates otherwise. As used herein, the terms "and/or" and "at least one of" include any and all combinations of one or more of the associated listed items. It will be further understood that the terms "comprises," "comprising," "includes," and/or "including," when used herein, specify the presence of stated features, integers, steps, operations, elements, and/or components, but do not preclude the presence or addition of one or more other features, integers, steps, operations, elements, components, and/or groups thereof. As used herein, the term "and/or" includes any and all combinations of one or more of the associated listed items. Expressions such as "at least one of," when preceding a list of elements, modify the entire list of elements and do not modify the individual elements of the list. Also, the term "example" is intended to refer to an example or illustration.

When an element is referred to as being "on," "connected to," "coupled to," or "adjacent to," another element, the element may be directly on, connected to, coupled to, or adjacent to, the other element, or one or more other intervening elements may be present. In contrast, when an element is referred to as being "directly on," "directly connected to," "directly coupled to," or "immediately adjacent to," another element there are no intervening elements present.

It should also be noted that in some alternative implementations, the functions/acts noted may occur out of the order noted in the figures. For example, two figures shown in succession may in fact be executed substantially concurrently or may sometimes be executed in the reverse order, depending upon the functionality/acts involved.

Unless otherwise defined, all terms (including technical and scientific terms) used herein have the same meaning as commonly understood by one of ordinary skill in the art to which example embodiments belong. It will be further understood that terms, e.g., those defined in commonly used dictionaries, should be interpreted as having a meaning that is consistent with their meaning in the context of the relevant art and will not be interpreted in an idealized or overly formal sense unless expressly so defined herein.

Before discussing example embodiments in more detail, it is noted that some example embodiments may be described with reference to acts and symbolic representations of operations (e.g., in the form of flow charts, flow diagrams, data flow diagrams, structure diagrams, block diagrams, etc.) that may be implemented in conjunction with units and/or devices discussed in more detail below. Although discussed in a particularly manner, a function or operation specified in a specific block may be performed differently from the flow specified in a flowchart, flow diagram, etc. For example, functions or operations illustrated as being performed serially in two consecutive blocks may actually be performed simultaneously, or in some cases be performed in reverse order. Although the flowcharts describe the operations as sequential processes, many of the operations may be performed in parallel, concurrently or simultaneously. In addition, the order of operations may be re-arranged. The processes may be terminated when their operations are completed, but may also have additional steps not included in the figure. The processes may correspond to methods, functions, procedures, subroutines, subprograms, etc.

Specific structural and functional details disclosed herein are merely representative for purposes of describing example embodiments of the present invention. This invention may, however, be embodied in many alternate forms and should not be construed as limited to only the embodiments set forth herein.

Units and/or devices according to one or more example embodiments may be implemented using hardware, software, and/or a combination thereof. For example, hardware devices may be implemented using processing circuitry such as, but not limited to, a processor, Central Processing Unit (CPU), a controller, an arithmetic logic unit (ALU), a digital signal processor, a microcomputer, a field programmable gate array (FPGA), a System-on-Chip (SoC), a programmable logic unit, a microprocessor, or any other device capable of responding to and executing instructions in a defined manner. Portions of the example embodiments and corresponding detailed description may be presented in terms of software, or algorithms and symbolic representations of operation on data bits within a computer memory. These descriptions and representations are the ones by which those of ordinary skill in the art effectively convey the substance of their work to others of ordinary skill in the art. An algorithm, as the term is used here, and as it is used generally, is conceived to be a self-consistent sequence of steps leading to a desired result. The steps are those requiring physical manipulations of physical quantities. Usually, though not necessarily, these quantities take the form of optical, electrical, or magnetic signals capable of being stored, transferred, combined, compared, and otherwise manipulated. It has proven convenient at times, principally for reasons of common usage, to refer to these signals as bits, values, elements, symbols, characters, terms, numbers, or the like.

It should be borne in mind, however, that all of these and similar terms are to be associated with the appropriate physical quantities and are merely convenient labels applied to these quantities. Unless specifically stated otherwise, or as is apparent from the discussion, terms such as "processing" or "computing" or "calculating" or "determining" of "displaying" or the like, refer to the action and processes of a computer system, or similar electronic computing device/hardware, that manipulates and transforms data represented as physical, electronic quantities within the computer system's registers and memories into other data similarly represented as physical quantities within the computer system memories or registers or other such information storage, transmission or display devices.

In this application, including the definitions below, the term 'module' or the term 'controller' may be replaced with the term 'circuit.' The term 'module' may refer to, be part of, or include processor hardware (shared, dedicated, or group) that executes code and memory hardware (shared, dedicated, or group) that stores code executed by the processor hardware.

The module may include one or more interface circuits. In some examples, the interface circuits may include wired or wireless interfaces that are connected to a local area network (LAN), the Internet, a wide area network (WAN), or combinations thereof. The functionality of any given module of the present disclosure may be distributed among multiple modules that are connected via interface circuits. For example, multiple modules may allow load balancing. In a further example, a server (also known as remote, or cloud) module may accomplish some functionality on behalf of a client module.

Software may include a computer program, program code, instructions, or some combination thereof, for independently or collectively instructing or configuring a hardware device to operate as desired. The computer program and/or program code may include program or computer-readable instructions, software components, software modules, data files, data structures, and/or the like, capable of being implemented by one or more hardware devices, such as one or more of the hardware devices mentioned above. Examples of program code include both machine code produced by a compiler and higher level program code that is executed using an interpreter.

For example, when a hardware device is a computer processing device (e.g., a processor, Central Processing Unit (CPU), a controller, an arithmetic logic unit (ALU), a digital signal processor, a microcomputer, a microprocessor, etc.), the computer processing device may be configured to carry out program code by performing arithmetical, logical, and input/output operations, according to the program code. Once the program code is loaded into a computer processing device, the computer processing device may be programmed to perform the program code, thereby transforming the computer processing device into a special purpose computer processing device. In a more specific example, when the program code is loaded into a processor, the processor becomes programmed to perform the program code and operations corresponding thereto, thereby transforming the processor into a special purpose processor.

Software and/or data may be embodied permanently or temporarily in any type of machine, component, physical or virtual equipment, or computer storage medium or device, capable of providing instructions or data to, or being interpreted by, a hardware device. The software also may be distributed over network coupled computer systems so that the software is stored and executed in a distributed fashion. In particular, for example, software and data may be stored by one or more computer readable recording mediums, including the tangible or non-transitory computer-readable storage media discussed herein.

Even further, any of the disclosed methods may be embodied in the form of a program or software. The program or software may be stored on a non-transitory computer readable medium and is adapted to perform any one of the aforementioned methods when run on a computer device (a device including a processor). Thus, the non-transitory, tangible computer readable medium, is adapted to store information and is adapted to interact with a data processing facility or computer device to execute the program of any of the above mentioned embodiments and/or to perform the method of any of the above mentioned embodiments.

Example embodiments may be described with reference to acts and symbolic representations of operations (e.g., in the form of flow charts, flow diagrams, data flow diagrams, structure diagrams, block diagrams, etc.) that may be implemented in conjunction with units and/or devices discussed in more detail below. Although discussed in a particularly manner, a function or operation specified in a specific block may be performed differently from the flow specified in a flowchart, flow diagram, etc. For example, functions or operations illustrated as being performed serially in two consecutive blocks may actually be performed simultaneously, or in some cases be performed in reverse order.

According to one or more example embodiments, computer processing devices may be described as including various functional units that perform various operations and/or functions to increase the clarity of the description. However, computer processing devices are not intended to be limited to these functional units. For example, in one or more example embodiments, the various operations and/or functions of the functional units may be performed by other ones of the functional units. Further, the computer processing devices may perform the operations and/or functions of the various functional units without subdividing the operations and/or functions of the computer processing units into these various functional units.

Units and/or devices according to one or more example embodiments may also include one or more storage devices. The one or more storage devices may be tangible or non-transitory computer-readable storage media, such as random access memory (RAM), read only memory (ROM), a permanent mass storage device (such as a disk drive), solid state (e.g., NAND flash) device, and/or any other like data storage mechanism capable of storing and recording data. The one or more storage devices may be configured to store computer programs, program code, instructions, or some combination thereof, for one or more operating systems and/or for implementing the example embodiments described herein. The computer programs, program code, instructions, or some combination thereof, may also be loaded from a separate computer readable storage medium into the one or more storage devices and/or one or more computer processing devices using a drive mechanism. Such separate computer readable storage medium may include a Universal Serial Bus (USB) flash drive, a memory stick, a Bluray/DVD/CD-ROM drive, a memory card, and/or other like computer readable storage media. The computer programs, program code, instructions, or some combination thereof, may be loaded into the one or more storage devices and/or the one or more computer processing devices from a remote data storage device via a network interface, rather than via a local computer readable storage medium. Additionally, the computer programs, program code, instructions, or some combination thereof, may be loaded into the one or more storage devices and/or the one or more processors from a remote computing system that is configured to transfer and/or distribute the computer programs, program code, instructions, or some combination thereof, over a network. The remote computing system may transfer and/or distribute the computer programs, program code, instructions, or some combination thereof, via a wired interface, an air interface, and/or any other like medium.

The one or more hardware devices, the one or more storage devices, and/or the computer programs, program code, instructions, or some combination thereof, may be specially designed and constructed for the purposes of the example embodiments, or they may be known devices that are altered and/or modified for the purposes of example embodiments.

A hardware device, such as a computer processing device, may run an operating system (OS) and one or more software applications that run on the OS. The computer processing device also may access, store, manipulate, process, and create data in response to execution of the software. For simplicity, one or more example embodiments may be exemplified as a computer processing device or processor; however, one skilled in the art will appreciate that a hardware device may include multiple processing elements or processors and multiple types of processing elements or processors. For example, a hardware device may include multiple processors or a processor and a controller. In addition, other processing configurations are possible, such as parallel processors.

The computer programs include processor-executable instructions that are stored on at least one non-transitory computer-readable medium (memory). The computer programs may also include or rely on stored data. The computer programs may encompass a basic input/output system (BIOS) that interacts with hardware of the special purpose computer, device drivers that interact with particular devices of the special purpose computer, one or more operating systems, user applications, background services, background applications, etc. As such, the one or more processors may be configured to execute the processor executable instructions.

The computer programs may include: (i) descriptive text to be parsed, such as HTML (hypertext markup language) or XML (extensible markup language), (ii) assembly code, (iii) object code generated from source code by a compiler, (iv) source code for execution by an interpreter, (v) source code for compilation and execution by a just-in-time compiler, etc. As examples only, source code may be written using syntax from languages including C, C++, C #, Objective-C, Haskell, Go, SQL, R, Lisp, Java®, Fortran, Perl, Pascal, Curl, OCaml, Javascript®, HTML5, Ada, ASP (active server pages), PHP, Scala, Eiffel, Smalltalk, Erlang, Ruby, Flash®, Visual Basic®, Lua, and Python®.

Further, at least one embodiment of the invention relates to the non-transitory computer-readable storage medium including electronically readable control information (processor executable instructions) stored thereon, configured in such that when the storage medium is used in a controller of a device, at least one embodiment of the method may be carried out.

The computer readable medium or storage medium may be a built-in medium installed inside a computer device main body or a removable medium arranged so that it can be separated from the computer device main body. The term computer-readable medium, as used herein, does not encompass transitory electrical or electromagnetic signals propagating through a medium (such as on a carrier wave); the term computer-readable medium is therefore considered tangible and non-transitory. Non-limiting examples of the non-transitory computer-readable medium include, but are not limited to, rewriteable non-volatile memory devices (including, for example flash memory devices, erasable programmable read-only memory devices, or a mask read-only memory devices); volatile memory devices (including, for example static random access memory devices or a dynamic random access memory devices); magnetic storage media (including, for example an analog or digital magnetic tape or a hard disk drive); and optical storage media (including, for example a CD, a DVD, or a Blu-ray Disc). Examples of the media with a built-in rewriteable non-volatile memory, include but are not limited to memory cards; and media with a built-in ROM, including but not limited to ROM cassettes; etc. Furthermore, various information regarding stored images, for example, property information, may be stored in any other form, or it may be provided in other ways.

The term code, as used above, may include software, firmware, and/or microcode, and may refer to programs, routines, functions, classes, data structures, and/or objects. Shared processor hardware encompasses a single microprocessor that executes some or all code from multiple modules. Group processor hardware encompasses a microprocessor that, in combination with additional microprocessors, executes some or all code from one or more modules. References to multiple microprocessors encompass multiple microprocessors on discrete dies, multiple microprocessors on a single die, multiple cores of a single microprocessor, multiple threads of a single microprocessor, or a combination of the above.

Shared memory hardware encompasses a single memory device that stores some or all code from multiple modules. Group memory hardware encompasses a memory device that, in combination with other memory devices, stores some or all code from one or more modules.

The term memory hardware is a subset of the term computer-readable medium. The term computer-readable medium, as used herein, does not encompass transitory electrical or electromagnetic signals propagating through a medium (such as on a carrier wave); the term computer-readable medium is therefore considered tangible and non-transitory. Non-limiting examples of the non-transitory computer-readable medium include, but are not limited to, rewriteable non-volatile memory devices (including, for example flash memory devices, erasable programmable read-only memory devices, or a mask read-only memory devices); volatile memory devices (including, for example static random access memory devices or a dynamic random access memory devices); magnetic storage media (including, for example an analog or digital magnetic tape or a hard disk drive); and optical storage media (including, for example a CD, a DVD, or a Blu-ray Disc). Examples of the media with a built-in rewriteable non-volatile memory, include but are not limited to memory cards; and media with a built-in ROM, including but not limited to ROM cassettes; etc. Furthermore, various information regarding stored images, for example, property information, may be stored in any other form, or it may be provided in other ways.

The apparatuses and methods described in this application may be partially or fully implemented by a special purpose computer created by configuring a general purpose computer to execute one or more particular functions embodied in computer programs. The functional blocks and flowchart elements described above serve as software specifications, which can be translated into the computer programs by the routine work of a skilled technician or programmer.

Although described with reference to specific examples and drawings, modifications, additions and substitutions of example embodiments may be variously made according to the description by those of ordinary skill in the art. For example, the described techniques may be performed in an order different with that of the methods described, and/or components such as the described system, architecture, devices, circuit, and the like, may be connected or combined to be different from the above-described methods, or results may be appropriately achieved by other components or equivalents.

Accordingly, a first embodiment of the present invention is directed to a system for supporting evaluation of a medical image data set. The system comprises several units. The system comprises an interface unit and a computing unit.

The interface unit is configured to
 provide a display of a medical image data set to a user,
 visualize an evaluation tool wherein the evaluation tool is adapted
  to be movably arranged in the displayed image data set, and
  to provide at least two evaluation functions with respect to the displayed image data set,
 visualize at least one result of an evaluation function
 receive user input relating to
  navigating the evaluation tool in the medical image data set to a region of interest, and
 selecting at least one of the evaluation functions.

The computing unit is configured to
 process the user input to
  navigate the evaluation tool in the medical image data set to the region of interest,
  perform the at least one evaluation function, wherein performing the at least one evaluation function comprises accounting for image data within the region of interest, and
  generate a visualization of at least one result of the evaluation function.

Another embodiment of the present invention is directed to a computer-implemented method for supporting evaluation of a medical image data set. The method comprises several steps.

A first step is directed to providing a display of a medical image data set to a user. A further step is directed to visualizing an evaluation tool adapted
 to be movably arranged in the displayed image data set, and
 to provide at least two evaluation functions with respect to the displayed image data set.

A further step is directed to receiving user input relating to navigating the evaluation tool in the medical image data set to a region of interest and to selecting at least one of the evaluation functions. A further step is directed to processing the user input to
 navigate the evaluation tool in the medical image data set to the region of interest and
 perform the at least one evaluation function.

Another step is directed to generating a visualization of at least one result of the evaluation function. And a further step is directed to visualizing the result of the evaluation function.

Both system and method embodiments are characterized in that the performing the at least one evaluation function comprises performing the evaluation function at least with respect to image data within the region of interest. Furthermore, embodiments of the present invention are characterized in that the at least one result presented to a user as an overlay to the displayed image data set and/or evaluation tool.

In other words, it is an idea of at least one embodiment of the present invention to provide an easy-to-use image evaluation/analysis tool for a user, which may be arbitrarily positioned in or on or over a displayed image data set. The evaluation/analysis tool thus allows the user to easily select a position or region of interest in the displayed image volume by directly moving the tool to this position. The evaluation tool, when positioned at the region of interest, is adapted to provide a plurality of different evaluation/analysis functions for the user to select, wherein each of the evaluation functions is adapted to provide evaluation/analysis results referring to image data within the selected position. Furthermore, at least one embodiment of the invention provides for a graphical user interface which is adapted to parallelly visualize medical image data, a palette of evaluation functions and evaluation results.

The computing unit can be realized as a data processing system or as a part of a data processing system. Such a data processing system can, for example, comprise a cloud-computing system, a computer network, a computer, a tablet computer, a smartphone and/or the like. The computing unit can comprise hardware and/or software. The hardware can be, for example, a processor system, a memory system and combinations thereof. The hardware can be configurable by the software and/or be operable by the software. Generally, all units, sub-units or modules may be at least temporarily be in data exchange with each other, e.g., via a network connection or respective interfaces. Consequently, individual units may be located apart from each other, especially the evaluation unit may be located apart, from the interface unit.

The interface unit may be understood as a mobile device, tablet, display screen or alternatively as a (radiology) workstation including its display screen. The interface unit enables data output for a user and is adapted to receive user input. Also, the interface unit may be configured to comprise a communication unit for data exchange with a local server or a central web server via internet connection.

The computing unit and an interface unit may as such be physically detached from each other and may preferably be located at different locations. However, alternatively, both units may be realized at least in parts physically integrated.

The medical image data set may be a two- or three-dimensional medical image data set that provides for image data e.g. in two or three spatial dimensions and thus corresponds to an image slice or volume. Alternatively, the three-dimensional image data set provides for image data with two spatial dimensions and another time dimension. The medical image data set may likewise correspond to a four-dimensional image data set comprising three spatial and another time dimension.

Alternatively, the medical image data set may comprise two or three spatial dimensions and one additional dimension, e.g. image contrast or (average) x-ray energy (e.g. dual computed tomography images). The medical image volume may depict a body part of a patient in the sense that it e.g. contains three-dimensional image data of a patient's body part or two-dimensional image data. Such medical data volumes may be acquired using a medical imaging modality. A medical imaging modality corresponds to a system used to generate or produce medical images. For example, a medical imaging modality may be a computed tomography system, a magnetic resonance system, an angiography (or C-arm X-ray) system, a positron-emission tomography system or the like, which are well known as such.

Specifically, computed tomography (CT) is a widely used imaging method and makes use of "hard" X-rays produced and detected by a specially rotating instrument. Magnetic Resonance Imaging (MRI) is an advanced diagnostic technique which makes use of the effect a magnetic field impacts on movements of protons. In MRI machines, the detectors are antennas and the signals are analyzed by a computer creating detailed images of the internal structures in any section of the human body. The medical image data set may comprise a plurality, i.e. at least two, preferably tens or hundreds of image slices (either in time or in space), each slice depicting a cross-section or a plane or a layer of the patient's imaged body region. The layers may be equidistantly spaced apart and oriented perpendicularly to a preferred viewing direction. With other words, the medical image data set may be an image stack in space or time or another dimension. Preferably, the image data set may comprise, continuous (three-dimensional) image information, e.g. generated by interpolation of anatomical structure information contained in the slices.

Firstly, a display of a medical image data set is provided to a user. With other words, the medical image volume is presented or visualized to the user via interface unit. The interface unit may thus comprise an output unit configured to display the medical image data set, i.e. generate a visual rendering of the medical image data set. The interface unit thus comprises at least, but also preferably one display screen. The display screen preferably has a high enough resolution and other display characteristics which enable the screen to be used for medical reading purposes. Displaying the medical image data set may comprise displaying one slice of the image stack (representing an specific anatomical position or point in time) or a projection image of image slices onto a preselected image plane. The medical image data set may be scrolled through slice by slice or the projection plane may be adapted to another view angle upon user request. The display of the image data set preferably comprises rendering the image element entries on a pre-defined grey scale, e.g. Houndsfield units for CT images. Usually, the imaging modality and protocol applied for image generation define an optimal and thus predefined greyscale as well as grey scale window.

At least one embodiment of the invention further provides a visualization of the evaluation and/or analysis tool via the display screen. The tool preferably has a predefined size and shape. However, both may be adapted according to user preferences or specific requirements of the displayed image data set based on corresponding user request or automatically. The evaluation tool may be automatically visualized as soon as an image evaluation software or application is started and/or the display of the medical image data set is requested or started by a user. However, the evaluation tool may also be deactivated, i.e. hidden and/or (re-) activated upon user request. The evaluation tool may be initially positioned in a preset default position, e.g. in one corner or the center of the displayed image data set.

According to a preferred embodiment of the present invention, the evaluation tool is adapted to be visualized as an overlay to the displayed image data set. The evaluation tool is visualized on top of, i.e. as a superposition to the displayed image data set. Precisely, the evaluation tool at least temporarily and at least partially covers or hides image elements, i.e. image pixels, at the position the evaluation tool is located at. With other words, the displayed medical image data set may not be visible at least temporarily where covered by the evaluation tool. The inventive evaluation tool is thus advantageously offered to the user in the context of the displayed image data set. The invention thus avoids lengthy searches for evaluation functions in well hidden evaluation menus or even other reading or evaluation applications.

The inventive evaluation tool of at least one embodiment is adapted to be moved, i.e. the tool may be moved over the displayed image data set. With other words, the tool position may be changed in the course of image evaluation, e.g. a radiologic reading procedure. Preferably, the tool position may be changed between different regions of interest. The movement preferably occurs upon user request, i.e. user input.

Accordingly, the interface unit comprises an input unit adapted to receive user input. The input unit may preferably comprise a mouse used to manipulate a cursor also displayed via display screen as an overlay to the displayed image data set and the evaluation tool. Movement of the evaluation tool may e.g. be performed by mouse click on a screen pixel presenting the tool and moving the mouse. Of course, alternative input units like touch pad, touch screen, microphone and/or keyboard are likewise possible and in the scope of the present invention. To sum up, the interface unit may further be understood as a device adapted to receive user input as regards at least one selected position or region of interest and/or an image slice or projection image to be displayed.

Accordingly, the computing unit may comprise a navigation unit configured to navigate the evaluation tool in the displayed medical image data set to the region of interest.

Most preferably, a region of interest, the evaluation tool may be moved to, comprises at least one abnormal or at least suspicious anatomical and/or structural feature, e.g. a cyst or a lesion or pathology, which needs detailed analysis to gain a profound radiologic result. Preferably, the region of interest covers additional neighboring tissue representing unsuspicious areas for providing additional contextual information. The region of interest may have an arbitrary shape, preferably the region of interest is of circular or quadratic form. However, the region of interest not necessarily covers a suspicious appearance or structure. Alternatively, the region of interest may correspond to any user-selected image part. The region of interest (ROI) may also be previously known, e.g. from prior studies or determined/identified upon initial automatic and/or user image analysis or visual inspection. A region of interest preferably comprises a plurality of image elements, i.e. pixels in the displayed image slice or projection image. Thus, the ROI may be two-dimensional. Alternatively, the ROI may be three-dimensional, e.g. by propagating the outer contours of the ROI in the displayed slice to other slices not displayed.

Preferably, the evaluation tool may be moved to a plurality of regions of interest in the course of a reading procedure. Accordingly, a user or an abnormality detection unit (as described later on) can, in the course of a reading procedure move from ROI to ROI by re-positioning (via user input), the evaluation tool. Thereby, not only one, but several image features may advantageously be analyzed and/or processed as laid out in the following.

The inventive evaluation tool of at least one embodiment is characterized in that it offers at least two evaluation functions which may be applied to the displayed image data set. An evaluation function may be any kind of computational image data analysis operation, like e.g. identifying, comparing, filtering, subtracting, adding, coloring, contouring, extracting individual image element entries. An evaluation function may likewise be to select and display the image date set according to another contrast setting or x-ray energy channel. At least two, preferably more evaluation functions may be offered for selection to the user when visualizing the evaluation tool. Thereby, the invention enables generation and/or acquisition of a plurality of information related to the displayed image data set, i.e. the selected region of interest without the need to access data (re-) sources other than the active user interface.

Upon the user selecting one of the evaluation functions, the evaluation tool performs at least one evaluation function by applying an analysis function to at least one image element entry, e.g. a grey value, preferably it is applied to a plurality of entries in the ROI. With other words, each evaluation function is specific for image content within the region of interest. Additionally, at least one evaluation function may comprise to further account for image element entries outside the region of interest.

The computing unit may thus comprise an evaluation unit configured to perform at least one evaluation function on image element entries within the region of interest. With other words, the present invention is based on the fact that the selected evaluation function considers at least one image element entry comprised in the region of interest. This leads to an evaluation result which is specific for the region of interest.

Preferably, the selected evaluation function is based on a plurality of image elements comprised in the selected position, i.e. the selected position in a displayed stack slice. However, the evaluation function may likewise consider further image elements not comprised in the selected position, not even comprised in the displayed image slice. To sum up, an evaluation function is performed by the inventive computing unit upon user request received via interface unit, for selecting at least one evaluation function to be performed.

The evaluation result may be in the form of adapted or manipulated image element entries. However, the evaluation result may likewise correspond to some kind of analysis results, wherein the analysis is conducted on image element entries, e.g. like time curves displaying a lesion growth, or certain values deduced from the image element entries, like size or diameter.

The computing unit may further comprise a visualization unit configured to generate a visualization (for a user) of at least one result of an evaluation function. This result may further be displayed to the user via the display screen of the interface unit. The result display is realized as an overlay, annotation or superimposition to the displayed image data set and/or the evaluation tool. With other words, also the evaluation result may be visualized to the user within the same graphical user interface. The evaluation result may comprise of integers, floating point numbers or even Boolean variables or graphical diagrams or curves based on the numbers or variables. In a step of visualizing, the evaluation result values may be translated or converted into a representation that can be readily assessed by the human eye, for instance. In other words, a visualization (a viewable representation) is generated (calculated) based on the result values. Further, the step of visualization may comprise a step of smoothing the degrees of similarity in order to allow for a more homogenous visualization.

Accordingly, the evaluation result may be visually rendered in the form of adapted image element entries. Alternatively, the evaluation result may be visually rendered in the form of textual or graphical overlays and/or additional evaluation result windows, e.g. for presenting a video superimposed on the displayed medical image data set.

Accordingly, at least one embodiment of the present invention combines image data display, a plurality of image data analysis/evaluation options each specific or tailored for selected regions of interest and the display of evaluation results in only one and the same graphical user interface. Thus, at least one embodiment of the invention avoids the need for the user to access or switch to several different data (re-)sources, e.g. other reading applications, other user interfaces, views, or even other (remote) databases, to gain evaluation results. This increases not only user comfort while reading, but also reading efficiency.

Computing and interface unit may both further comprise a communication unit adapted for bidirectional data exchange between each other, e.g. user requests as regards the selected position or evaluation function or evaluation results to be visualized to the user via the display screen. The computing unit may further be adapted to perform data exchange, preferably data retrieval from a local or central server via internet connection via the communication unit.

It goes without saying that embodiments of the present invention are not limited to one region of interest for one reading procedure. The full benefit of embodiments of the present invention is realized, when embodiments of the present invention is repeated numerous times for several regions of interest within the same image data set.

Another embodiment of the present invention is directed to a system, wherein the interface unit is further adapted to display the evaluation tool as a circular evaluation tool positioned as an overlay to the region of interest. A circular or round shape advantageously accounts for the typical appearance of plurality of suspicious or abnormal structures like cancerous lesions, lung nodules or cysts. Thus, the shape of the evaluation tool may advantageously be fit to the shape of a lesion or pathologic structure under examination. However, the shape of the evaluation tool may alternatively be adapted to other shapes like e.g. square shape or elliptic shape. With other words, the form of the evaluation tool may be adapted to correspond best to the shape of a lesion comprised in the selected position.

Another embodiment of the present invention is directed to a system, wherein the circular tool comprises at its center a transparent circular field of view adapted to cover the region of interest and at its circumference a rotatable ring subdivided into a plurality of ring segments, wherein each ring segment embodies an evaluation function, wherein an evaluation function is activatable by rotating the rotatable ring such that the ring segment corresponding to the evaluation function takes an activation position. This embodiment advantageously provides for a transparent viewing area, which allows inspection of image content of the displayed image data set, although the evaluation tool is already position at the region of interest. Preferably, the viewing area enables vision of a lesion or suspicious structure within the region of interest. This enables the user to select an evaluation function while inspecting the region of interest, this embodiment further enables the consecutive selection of more than one evaluation functions, while inspecting the region of interest. Thereby, time-consuming and cumbersome changes of user interfaces and/or screens is avoided.

The plurality of evaluation functions is distributed over a corresponding number of ring segments on the circumference of the circular tool disregarding the number of evaluation functions provided. This arrangement, in any case enables continuous visibility of anatomical structures under examination.

Rotating the ring (e.g. via activated mouse movement or via touch pad) until a ring segment corresponding to a selected function reaches an activation position corresponds to an intuitive, fast and easy method for selecting and/or activating an evaluation function. Of course, alternative function selection mechanisms are also possible without leaving the scope of the present invention.

An embodiment of the present invention is directed to a system, wherein at least one ring segment is further configured to, upon activation, generate an interactive operation menu comprising a plurality of operations related to the evaluation function. Preferably generation of the operation menu further comprises visualization of the operation menu as an overlay to the evaluation tool and/or the displayed image data set likewise avoiding, to open or access other user interfaces.

An embodiment of the present invention is directed to a system, wherein the computing unit is further configured to detect at least one abnormality in the image data set. With other words, the computing unit is adapted to automatically apply at least one computer-aided detection (CAD, also computer-aided diagnosis) algorithm to the image data set. CAD algorithms are adapted to process digital medical image data sets to identify atypical structures or appearances in order to assist users in interpreting the medical images and deduce a (radiologic) diagnose. CAD algorithms are typically based on artificial intelligence, e.g. they apply convolutional neural networks. The optional step of automatically identifying an abnormality may be detached from other inventive steps. The step of identifying an abnormality may preferably be performed prior to all other steps rather relating to a preparatory image preprocessing step, other evaluation steps are based on.

An embodiment of the present invention is directed to a system, wherein the interface unit is further adapted to highlight the detected abnormality. With other words, according to this embodiment an abnormality automatically detected by a CAD algorithm is visually emphasized for a user in the displayed image data set. Highlighting may be realized by replacing grey values for image elements or only the respective contour image elements identified to belong to an abnormality with color or unusual grey values. Alternatively, abnormalities may be visualized with textual or symbol labelling. Thereby, a user can easily recognize abnormalities while scrolling through an image data set and position the evaluation tool, accordingly.

A preferred embodiment of the present invention is directed to a system, wherein the interface unit is configured to automatically position the evaluation tool as an overlay to the highlighted abnormality. Thus, when opening or staring the reading application or corresponding graphical user interface, the image data set is visualized such that the abnormality can be seen by the user at first glance within the field of view of the evaluation tool corresponding to an initial visual guidance especially for unexperienced users. This procedure further implies that the image data set is displayed such that the abnormality is focused. For example, an image slice containing a representative sectional view of the abnormality may be chosen to be displayed or a projection view containing a projection of all image stack slices contributing to the abnormality.

In this embodiment, the user can right away start selecting evaluation functions relating to the displayed region of interest.

Another embodiment of the present invention is directed to a system, wherein performing the at least one evaluation function comprises generating as a result evaluation data and/or additional data wherein evaluation data are based on image data within the region of interest and additional data are at least related to image data within the region of interest and at least in parts retrieved from a data source. With other words, an evaluation result may comprise data or values which were calculated using at least one, preferably a plurality of image element values of the displayed image within the region of interest. The evaluation result may alternatively comprise additional data related to the region of interest, i.e. at least to one image element entry within the region of interest, preferably to more than one entry. Additional data are thus not calculated in the course of the reading procedure but are retrieved from a data source. Data retrieval however may comprise a step of extracting and/or searching for additional data specific for the at least one image element entry. For example, additional data may be searched based on a specific shape of a lesion in the region of interest or based on a position of a lesion with respect to a landmark position. A data source may be for example a local image database of a hospital, like a PACS (picture archiving and communication server) or an local storage system integrated in the computing or an (image) storage unit in the cloud, a hospital or radiology information system (HIS, RIS). Alternative data sources may be external data sources like external databases like Thieme database, medical knowledge databases or a similar patient search engine e.g. like described in patent application EP18189090. Alternatively, the evaluation result may comprise evaluation and additional data or a combination of both. Accordingly, there may be at least one evaluation function which generates an evaluation result based on both calculations on image element entries within the region of interest and additional data. This embodiment spans a wide range of evaluation functions, which may be applied according to the invention.

As already indicated above, additional data and evaluation data and/or image data as such, i.e. image element entries, may together be subject to further processing. In an embodiment of the present invention the computing unit is further configured to at least partially register image data within the region of interest with the evaluation and/or additional data. This registration step may be conducted as sub-step of a selected evaluation function and serve particularly to quantify structural differences between consecutive studies conducted on the same patient and/or simulated model-based prognosis data. For example, lesion growth or shrinkage may thus be monitored during or without treatment. Image registration techniques as such are well known in the art. It goes without saying that, generation of some of the evaluation results may further comprise a step of image segmentation, particularly the evaluation results, which further require image registration. Thus, a segmentation step may be conducted as sub-step of at least one evaluation function. Also image segmentation techniques as such are well known in the art.

Accordingly, in embodiments of the present invention, the evaluation and/or additional data may comprise at least one of the following group of data:
  reference medical image data of a prior study covering at least partially the region of interest,
  prognosis medical image data indicative of a disease progression the prognosis relating to the region of interest.

The display of both these evaluation results on top of the displayed image data set and/or the evaluation tool enables a direct visual comparison of a current state with a previous state of e.g. a lesion or with a prognosed future state of the lesion. Data retrieval from a plurality of data sources for further processing and/or display in the context of a specific reading procedure realizes comfortable and effective information integration.

Another embodiment of the present invention is directed to a system, wherein the evaluation and/or additional data may comprise at least one of the following group of data:
  a video of image data within the selected position (e.g. for vividly illustrating lesion growth),
  a three-dimensional view of image data within the region of interest (e.g. rotating video clip of a lesion over a small view angle),
  a magnified view of image data within the region of interest,
  an augmented view of image data within the selected position (e.g. applying a specific color coding, windowing or image contrast).

Inventive display of these evaluation results on top of the displayed image data set and on top of or as part of the evaluation tool provides additional, diagnostically valuable insights into the displayed image data set.

Another embodiment of the present invention is directed to a computer program product comprising program elements which induce a computing unit of a system for supporting evaluation of a medical image data set, to perform the steps according to an embodiment of the inventive method, when the program elements are loaded into a memory of the computing unit.

Another embodiment of the present invention is directed to a computer-readable medium on which program elements are stored that are readable and executable by a computing unit of a system for supporting evaluation of a medical image data set, in order to perform steps of an embodiment of the inventive method, when the program elements are executed by the computing unit.

The realization of the invention by a computer program product and/or a computer-readable medium has the advantage that already existing systems can be easily adopted by software updates in order to work as proposed by the invention.

The computer program product can be, for example, a computer program or comprise another element next to the computer program as such. This other element can be hardware, for example a memory device, on which the computer program is stored, a hardware key for using the computer program and the like, and/or software, for example a documentation or a software key for using the computer program. The computer program product may further comprise development material, a runtime system and/or databases or libraries. The computer program product may be distributed among several computer instances.

In summary, at least one embodiment of the present invention has the advantage that reading efficiency can be increased by speeding up access of relevant supplementary diagnostically relevant information for a user, e.g. a radiologist. User fatigue is reduced by providing an integrated user interface on top of the displayed image. Combination and close integration of the different components and data sources allow reduction and filtering out of relevant information and to provide context specific information where needed.

FIG. 1 depicts an inventive system 1 for performing at least one medical imaging procedure according to an embodiment of the present invention. The system is adapted to perform the inventive method according to one or more embodiments, e.g. as further described with reference to FIG. 5. The system comprises an interface unit 20 in the form of a reading workstation. The system 1 further comprises a computing unit 30 in the form of a processor comprising several subunits involved in performing the inventive method. The interface unit 20 comprises an output unit 21 and an input unit 22. The output unit is realized as a display screen, preferably a 5$k$ display screen providing high resolution and thus enabling visually reading medical images, e.g. in a radiology. Any other display screen is however possible, too as long as it complies with resolution and other visualization requirements, e.g. color fidelity, set up for displaying medical images for reading purposes. Output unit 21 is adapted to visualize a medical data set, i.e. a medical image providing three spatial dimensions. The medical image data set MEDI may relate to an examination using an imaging modality of a body part of a patient. For example, the output unit 21 may visualize a selected image slice out of the image data set or a projection image comprising image information of a plurality of image slices.

The display of the data set may comprise the presentation of tissue TIS in the examined body part of a patient under examination. The presented tissue TIS may comprise a suspicious or pathologic or abnormal structure, i.e. a lesion LES, which is likewise presented via output unit 21. A region of interest ROI is defined by at least the area covered by the lesion LES, preferably a slightly bigger area. The output unit 21 is further adapted to visualize an inventive evaluation tool 40 on the display screen. Preferably, the evaluation tool 40 is visualized as an overlay to the medical image data set MEDI, and most preferably to the region of interest ROI covering the lesion LES.

The evaluation tool 40 comprises a field of view 44 for enabling a user to see/inspect the image information underneath. The displayed evaluation tool 40 further comprises an area 43, here ring-shaped, which temporarily conceals the image information underneath. Area 30 may be of other than circular shapes as well and comprises the display of at least two evaluation functions EVA1, EVA2, which may be selected and/or activated by a user. The output unit 21 is adapted to visualize the evaluation tool 40 in different shapes, sizes and operation states, which will be described in more detail with respect to FIGS. 2, 3 and 5. However, the output unit 21 is also adapted to present on the display screen an evaluation result window 45 which comprises at least one evaluation result RES.

The result window 45 is preferably presented as an overlay to the displayed medical image data set MEDI and/or the evaluation tool 40. For example, the result window 45 may be positioned as an overlay to the field of view 44 and thus have the same shape as the field of view 44. Accordingly, an evaluation result RES may be presented as part of the evaluation tool 40.

In FIG. 1, the result window 45 is displayed next to the evaluation tool 40. The output unit 21 is further adapted to present on the display screen at least one operation menu 46 (cf. FIG. 4) of the evaluation tool 40. The operation menu 46 may likewise be displayed as an overlay to the medical image data set MEDI and/or the evaluation tool 40. The evaluation tool 40 is adapted to be moved within the display screen, i.e. between different positions.

The interface unit 20 thus further comprises an input unit 22 for receiving user input relating to navigating the evaluation tool 40 in the displayed image, preferably to a region of interest ROI. Here the input unit 22 is realized in the form of a computer mouse, corresponding cursor and a keyboard. The evaluation tool may e.g. be navigated by clicking and moving the mouse. The input unit 22 is further adapted to receive a selection of at least one evaluation function EVA of the evaluation tool 40. For example, each evaluation function EVA may for selection and/or activation be assigned a key of the keyboard.

Summing up, the output unit 21 may be adapted to graphically visualize a graphical user interface for medical image reading. Furthermore, the output unit 21 may be adapted to visualize an evaluation tool 40. The input unit 22 may be adapted to receive user input as regards tool navigation and/or evaluation function selection. Accordingly, the interface unit 20 may comprise an LCD, plasma or OLED screen or display. It can also comprise a touch-sensitive screen, a keyboard, a mouse, or a microphone and loudspeaker. Accordingly, the interface unit 20 may further comprise respective processing units adapted e.g. for providing a graphical user interface as laid out above, for displaying a medical image data set MEDI and/or for processing input received from user. These processing units, according to FIG. 1, are provided as subunits to the computing unit. With other words. Computing unit 30 and interface unit 20 may be at least in parts form a physical entity.

The computing unit 30 is adapted to process the user input received via the interface unit 20. In detail the computing unit 30 is adapted to process the user input to navigate the evaluation tool 40 to a selected position, e.g. the region of interest ROI. The computing unit 30 is further adapted to perform at least one selected evaluation function EVA and generate at least one evaluation result RES. The computing unit 30 is also adapted to generate a visualization representation of the evaluation result RES.

Accordingly, the computing unit 30 comprises a navigation unit 31, which is adapted to instantaneously process the user input as regards the tool navigation to arrange it at a new position. The computing unit 30 further comprises an evaluation unit 32 configured to perform at least one selected evaluation function EVA. Thus, the evaluation 32 unit is adapted to perform mathematical calculations on individual image element entries of the image data set, especially of image elements comprised in the region of interest ROI. The computing unit 30 may further comprise a visualization unit 33 configured to generate a visualization representation of the evaluation result RES for display on via output unit 21. The computing unit 30 may optionally comprise an abnormality detection unit 36 adapted to automatically detect or identify areas or structures in the medical image data set MEDI showing suspicious or abnormal or disease imaging properties, like e.g. lesions or cysts. The abnormality detection unit 36 may apply well known computer-aided detection algorithms for medical image data. The computing unit 30 may further comprise a storage unit 35 adapted to at least temporarily store evaluation results and/or additional data, each being retrievable for either display or further processing in the course of performing an evaluation function.

The computing unit 30 and/or individual subunits 31, 32, 33 may comprise either a computer/processing unit, a microcontroller or an integrated circuit. Alternatively, the computing unit 30 may comprise a real or virtual group of computers like a so called 'cluster' or 'cloud'. The server system may be a central server, e.g. a cloud server, or a local server, e.g. located on a hospital or radiology site.

Computing unit 30 and interface unit 20, but also individual subunits of the computing unit 30 may be at least temporarily connected to each other for data transfer and/or exchange. Interface unit 20 communicates with computing unit 30 via communication units 24 and 34. Communication may comprise transfer e.g. of a visual rendering of a medical image data set MEDI for display to the user, image element entries, signals corresponding to user input or transfer of evaluation results for presentation via output unit 21. For example, navigation unit 31 may be activated on a request-base, wherein the request is sent by the interface unit 20. Evaluation unit 32 may further communicate with storage 35 or a remote database via corresponding interfaces. Here, additional data are retrieved for display and/or further processing. Storage 35 may likewise be activated on a request-base, wherein the request is sent by the evaluation unit 32.

Subunits 31, 32, 33 may be integrated to form one single unit or can be embodied by computer code segments configured to execute the corresponding method steps running on a processor. Each subunit 31, 32, 33 may be individually connected to other subunits and or other components of system 1 where data exchange is needed to perform the method steps. For example, visualization unit 33 may be connected to storage unit 35 for retrieving the medical image data set MEDI on to interface unit 20 for forwarding/showing the visual representation of the medical image data set MEDI to a user via output unit 21.

Storage unit 35 may generally be configured for acquiring and/or storing and/or forwarding medical image data sets MEDI. Storage unit 35 may comprise an archive/review station for storing medical image data sets MEDI. Archive/review station may be realized as a cloud storage. Alternatively, archive/review station may be realized as a local or spread storage, e.g., as a PACS (Picture Archiving and Communication System). Archive/review station may further store further clinical information related to the medical image data sets MEDI, wherein the clinical information may comprise, e.g., related medical findings, personal information related to the patient under consideration, patient records or the like. Alternatively, a further database (not shown) may store this related information.

An interface for data exchange, also communication units 24, 34 may be realized as hardware- or software-interface, e.g. a PCI-bus, USB or firewire. Subunits 31, 32, 33 of the computing unit 30 may comprise a hardware or software component e.g. a micro-processor or a FPGA ('Field Programmable Gate Array). Storage unit 35, e.g. a database may be realized as Random Access Memory (RAM), as durable mass storage (hard drive), solid state disk or the like.

Data transfer preferably is realized using a network connection. The network may be realized as local area network (LAN), e.g. an intranet or a wide area network (WAN). Network connection is preferably wireless, e.g. as wireless LAN (WLAN or WiFi). The network may comprise a combination of different network examples. Data transfer may be bidirectional.

Specifically, the network may comprise a network compatible with the DICOM-standard (Digital Imaging and Communications in Medicine) and the retrieval of the medical image data set MEDI may be carried out by a DICOM query and retrieve application class. Likewise, archiving an evaluation result in Storage unit 35 may be carried out using the DICOM query and retrieve application class.

Computing unit 30 may also be integrated in interface unit 20. As already mentioned, computing unit 30 may alternatively be embodied as a server system, e.g., a cloud server, or a local server, e.g., located on a hospital or radiology site. In this constellation, interface unit 20 could be designated as "frontend" or "client" facing the user, while computing unit 20 could correspond the "backend" or server. Communication between interface unit 20 and computing unit 30 may be carried out using the https-protocol, for instance. The computational power of the system may be distributed between the server and the client. In a "thin client" system, the majority of the computational capabilities exists at the server. In a "thick client" system, more of the computational capabilities, and possibly data, exist on the client.

Figure 2:
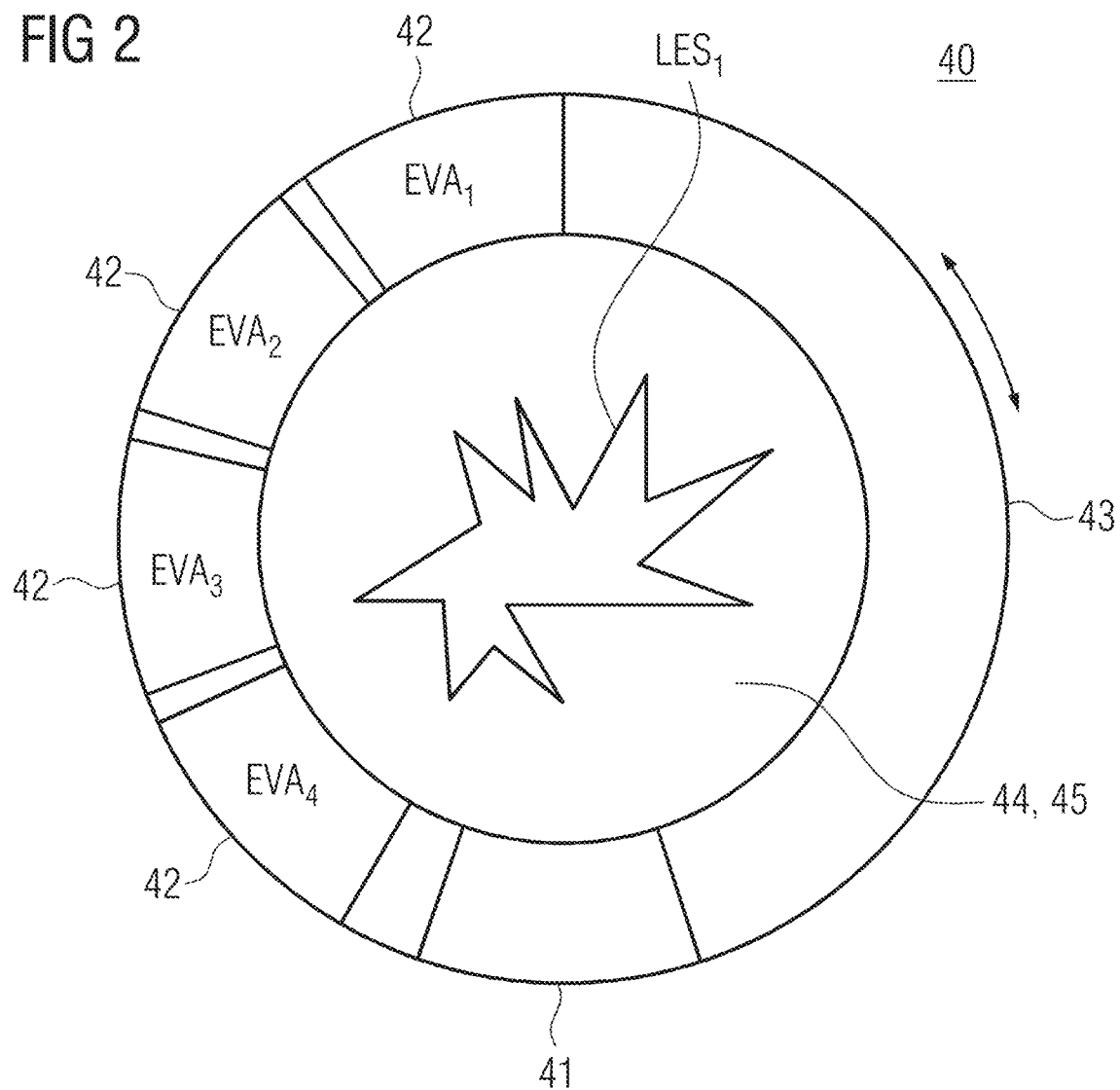
FIG. 2 depicts an inventive evaluation tool according to an embodiment of the present invention in a first operation state.

FIG. 2 depicts an inventive evaluation tool 40 according to an embodiment of the present invention in a first operation state. This operation state corresponds to an initial state, the evaluation tool 40 is in, when the tool is initially visualized, e.g. according to step S2 of the inventive method, as described in more detail with respect to FIG. 5. The evaluation tool 40 is depicted here is visualized on or via display screen 21. The evaluation tool 40 is displayed as an overlay to a displayed medical image data set MEDI. For illustration purposes, display screen as well as medical image data set MEDI are not shown here except for lesion LES1.

The evaluation tool 40 of this embodiment comprises at its center a circular field of view 44. The field of view is transparent. With other words, anatomical structures comprised in the medical image data set MEDI displayed at the same time underneath the field of view 44, are visible via the field of view 44. Here, the evaluation tool 40 is positioned at a region of interest ROI comprising a lesion LES1, which is visible via field of view 44. Ring 43 at the circumference of the evaluation tool 40 comprises an activation area 41 or an activation position. This area 41 is stationary with respect to the ring 43. The ring 43 further comprises a plurality, i.e. at least two, here four ring segments 42, wherein each ring segment embodies a specific evaluation function EVA1, EVA2, EVA3, EVA4. The ring segments 2 are rotatably arranged such that the ring segments 42 may be rotated around a center point of the field of view 44 (illustrated by the bidirectional arrow), until one of the evaluation functions EVA1, EVA2, EVA3, EVA4 takes the activation position 41. In this embodiment, as soon as the evaluation function is positioned at the activation position 41 via rotating movement of the ring segments 42, the corresponding evaluation function is started.

Rotation of the ring segments may be realized by clicking on one of the ring segments and using the scrolling wheel of the computer mouse. Rotating the ring segments might likewise be replaced by clicking on one of the ring segments using the mouse cursor for choosing an evaluation function by the user.

Figure 3:
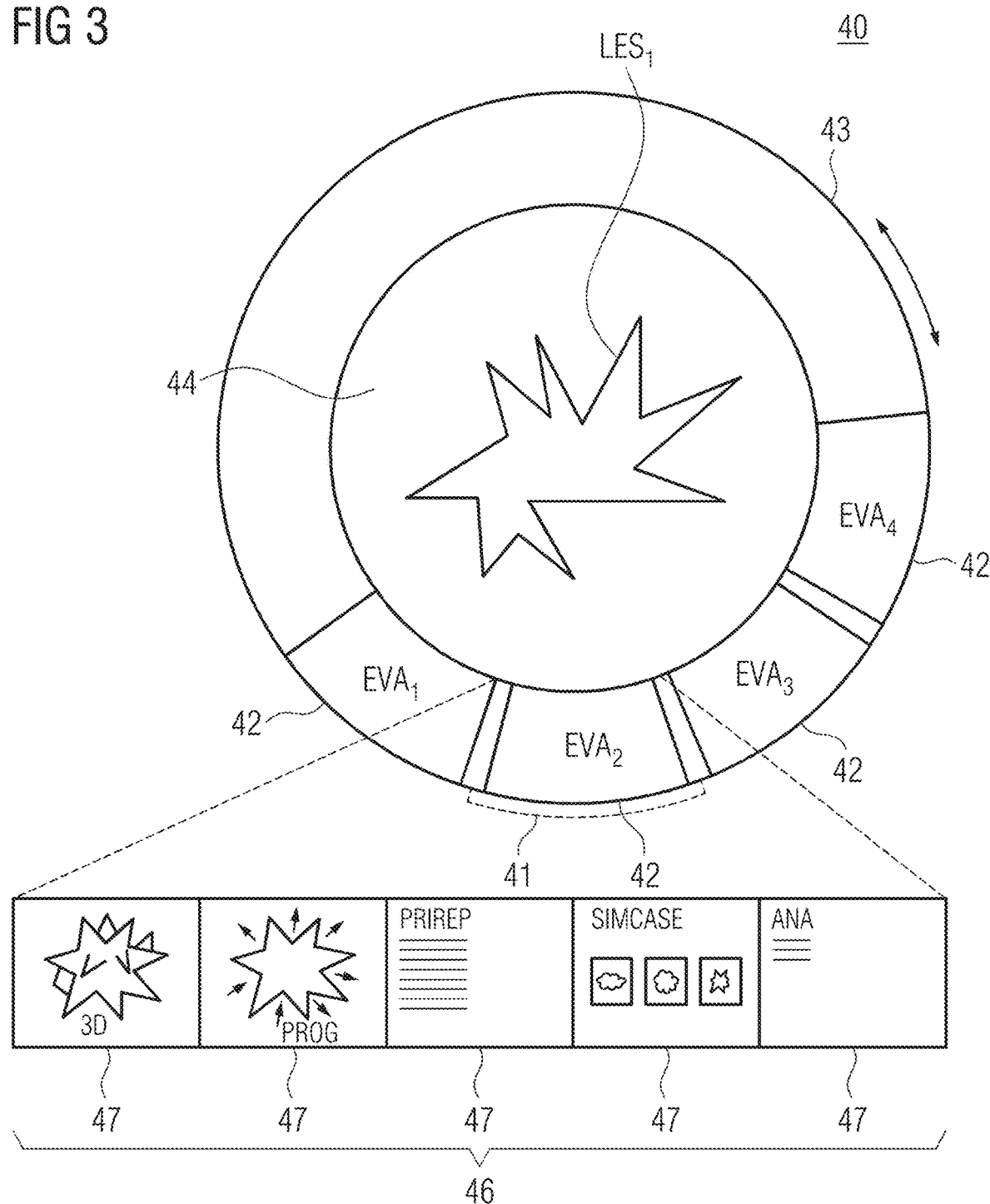
FIG. 3 depicts an inventive evaluation tool according to an embodiment of the present invention in a second operation state.

FIG. 3 depicts an inventive evaluation tool 40 according to the embodiment of FIG. 2 in a second operation state. This operation state corresponds to a state, the evaluation tool 40 is in, when an evaluation function EVA was selected, here evaluation function EVA2 (according to optional step S41 as described with respect to FIG. 5). Evaluation function EVA2 is the at least one evaluation function offering a plurality of different evaluation operations 47 to the user. Different, not necessarily all the evaluation operations 47, are offered to the user via the display of an operation menu 46. The operation menu 46 in this embodiment comprises a plurality of operation windows, each window embodying a different evaluation operation 47 which upon user selection may be performed on either image element entries and/or additional data. Preferably, as illustrated, each operation window may comprise a picture/symbol/textual indication of the purpose of the evaluation operation 47.

For example, one operation may be directed to calculating and/or providing based on the displayed medical data set a three-dimensional representation of lesion LES1, e.g. by providing a short video clip of two to ten projection views of lesion LES1, each projection view relating to a slightly different view angle (3D), thereby conveying a three-dimensional impression to the user. This evaluation operation would require a full segmentation of the lesion LES1 within the displayed image data set and might imply data interpolation steps between imaging slices.

Another evaluation operation may be directed to providing an image series representing lesion growth or shrinkage (PROG) over time. This evaluation operation implies acquisition of additional data in the form of prior study images from e.g. a storage unit 35, and segmentation/registration steps between different consecutive data sets. The acquisition of additional data is conducted under consideration of at least one image element entry within the region of interest ROI. This evaluation operation might further comprise quantification and color-coding of volume/size changes over time in the image series. The image series might be toggled through in both directions in time, e.g. via mouse scroll wheel or the like, thereby highlighting the changes over time. Also, the image series might be presented to the user as an overlay to the field of view 44. Other evaluation operations might by acquiring and presenting to the user at least part of prior reports of the patient under examination (PRIREP) or a textual representation of a lesion analysis/quantification (ANA) like diameter, volume, heterogeneity, presence of biomarkers and so forth. As a further alternative, an evaluation operation might acquire and present to the user similar lesions to lesion LES1 from other patients to enable differential diagnosis. Preferably, the search for similar lesions is based on an extracted image feature signature specific for the region of interest ROI.

It goes without saying that each individual evaluation operation 47 might be embodied as an evaluation function EVA as well. Accordingly, all example evaluation operations 47 might likewise correspond to evaluation functions. Of course, there are more functions/operations possible which are not explicitly mentioned here without leaving the scope of the present invention.

However, grouping evaluation operations 47 under one evaluation function EVA might be advantageous in those cases, e.g. where the number of evaluation operations 47 would require more and smaller ring segments 42 which would impede easy and fast operation of the evaluation tool 40. Apart from that grouping of evaluation operations 47 under one evaluation function might by performed topic-related. For example, operation functions 47 relating to or involving the acquisition and further processing of image data from prior studies of the patient under examination might be grouped under one evaluation function, to foster intuitive usage.

Figure 4:
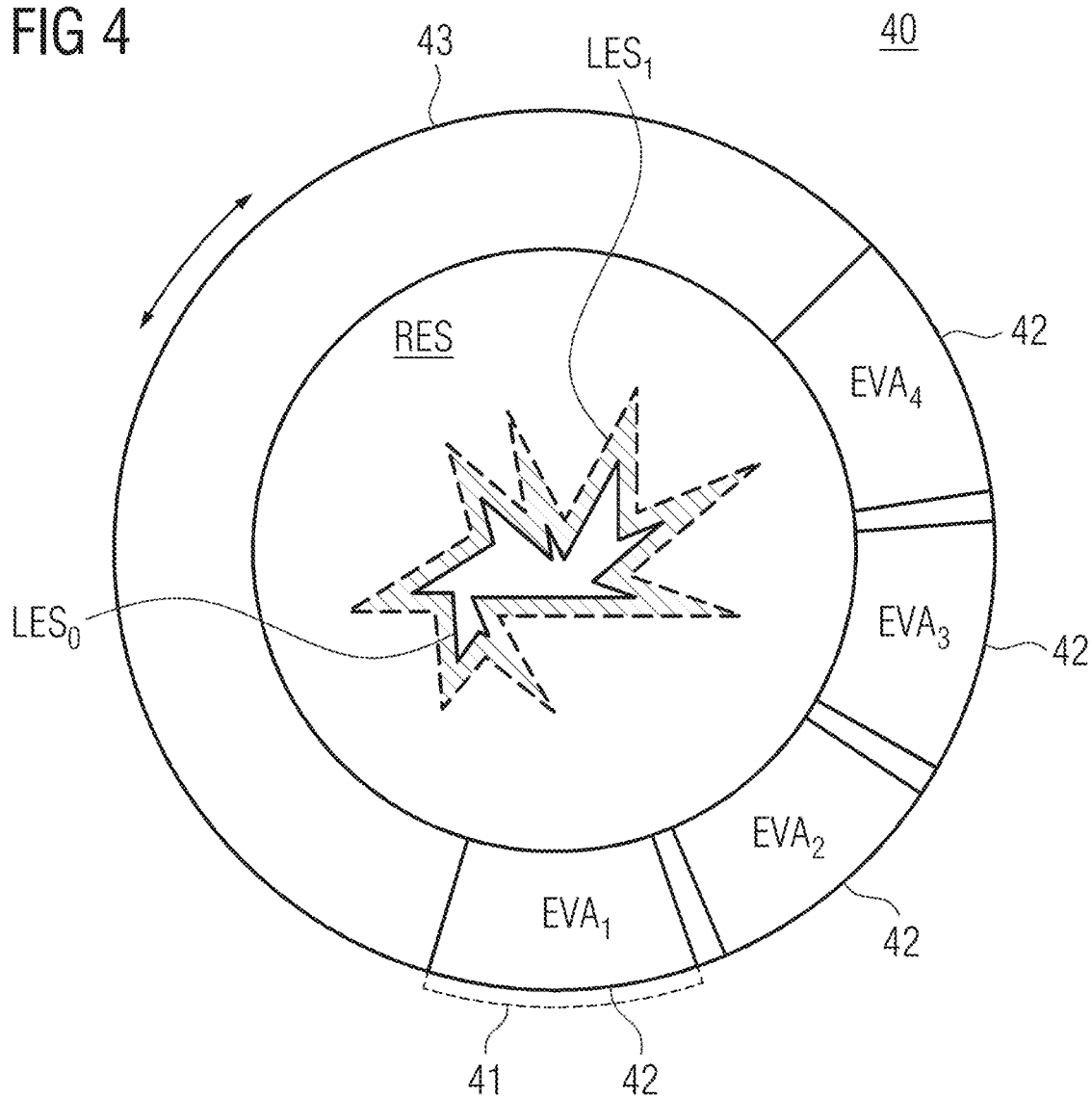
FIG. 4 depicts an inventive evaluation tool according to an embodiment of the present invention in a third operation state.

FIG. 4 depicts an inventive evaluation tool 40 according to an embodiment of the present invention in a third operation state. This operation state corresponds to a state, the evaluation tool 40 is in, when an evaluation function EVA was performed and an evaluation result RES is displayed to the user via output unit 21 (according to step S6 as described with respect to FIG. 5). In this operation state, the graphical user interface thus comprises a field or an area or window as result window 45 which comprises the evaluation result RES to be inspected by the user. In this preferable embodiment, an evaluation result RES e.g. in the form of a highlighted (color-coded, adapted contrast, magnified view or the like) medical image slice, a video clip or image series might be presented within the field of view 44 of the evaluation tool 40. Here, the evaluation result RES is visualized as an overlay to the field of view 44. Here, the evaluation result RES comprises an illustration using color coding of how much lesion LES1 has grown since a last examination. At that time, the lesion only had a size corresponding to LES0. Correspondingly, the dashed area within lesion LES1 illustrates lesion growth or change over time at one glance. Of course, alternatively, the evaluation result RES may be displayed at an arbitrary position within the display screen as an overlay to the displayed medical image data set MEDI as well.

FIG. 5 depicts an inventive method for supporting evaluation of a three-dimensional medical image data set MEDI according to an embodiment of the present invention. The inventive method comprises numerous steps. This method is a computer-implemented method.

In a step S1 a display of a three-dimensional medical image data set MEDI is provided to a user via an output unit 21. Preferably, one image slice of the medical data set MEDI is rendered according to typically applied greyscale window.

In a step S2 an evaluation tool 40 is visualized, too. The evaluation tool 40 may correspond to the one described with respect to FIGS. 2, 3 and 4. Visualization of the evaluation tool 40 is realized as an overlay, i.e. on top of the displayed medical image data set MEDI. Thus, the evaluation tool 40 at least temporarily hides some of the displayed image elements, i.e. pixels. In one alternative, the evaluation tool 40 may be initially displayed at a preset position within the graphical user interface. For example, the initial position may be at one of the corners of the display screen. The initial position may also be changed or adapted according to user preferences while configuring or setting up the reading application. The inventive evaluation tool 40 is adapted to be movably arranged in the displayed image data set 40 and to provide at least two evaluation functions EAV with respect to the displayed image data set MEDI. With other words, the evaluation tool can be moved around based on user request and corresponding input via input unit 22. Furthermore, display of the evaluation tool 40 comprises the display of at least two evaluation functions EVA as described with respect to FIGS. 3 and 4.

In an optional step S0 at least one abnormality, e.g. LES1, may be detected in the displayed image data set MEDI. Step S0 may be conducted prior to any of steps S1 or S2. Step S0 may preferably be conducted by computing unit 30, preferably abnormality detection unit 36. Abnormality detection may comprise applying at least one computer aided detection algorithm to the medical image data set MEDI. Abnormality detection may likewise comprise application of a convolutional neural network to the medical image data set MEDI. Step S0 may also comprise well known as such image segmentation steps.

Step S2 may, according to this option, comprise to automatically display the evaluation tool 40 as an overlay to the thus detected abnormality, i.e. as an overlay to the abnormality. Preferably, the abnormality is automatically centered in the transparent field of view 44 of the evaluation tool 40, like lesion LES1 is with respect to FIGS. 2, 3 and 4. By doing so, the user is visually led to inspect the abnormality. This is particularly advantageous in cases, where an abnormality might be overseen at first glance. As a further alternative or in addition, step S2 may also comprise to visually highlight, e.g. by color coding or by adding a tag providing information on the detected abnormality. Thereby, the user instantaneously is provided diagnostically relevant information on the detected abnormality.

In a step S3 user input relating to navigating the evaluation tool 40 in the three-dimensional medical image data set MEDI to a region of interest ROI is received via input unit 22. Here, any kind of input device including microphone or gesture or eye movement control (using at least one camera), may serve for receiving the user input. Step S3 further comprising sending the signals received as user input to the computing unit 30, preferably navigation unit 31 and there processing the user input to navigate the evaluation tool 40 in the medical image data set MEDI to the region of interest ROI. With other words, navigation unit 31 calculated navigation orders according to moving the navigation tool 40 to a position desired by the user. Preferably, processing takes place instantaneously such that the user may, according to 'drag-and-drop' move the evaluation tool at a position he is wants to examine in detail.

In a step S4 at least one of the displayed evaluation functions EVA is selected. Accordingly, more than one evaluation function EVA can be selected, preferably, consecutively, when at least one result RES relating to a selected evaluation function EVA was already presented via output unit 21 to the user. Preferably, an evaluation result window 45 of a previously selected evaluation function EVA may be continued to be presented while another result RES of a further evaluation function EVA is also displayed. Accordingly, step S4 comprises to receive via input unit 22 and process via computing unit 30, preferably evaluation unit 32, user input as regards a desired evaluation function EVA. Selection of an evaluation function EVA further comprises sending an activation request from the interface unit 20 to the evaluation unit 32.

In an optional step S41 the selection of an evaluation function EVA activates the generation and visualization of an interactive operation menu 46 comprising a plurality of operations, i.e. operation functions 47 related to the evaluation function EVA. Accordingly, in this alternative, selection of an evaluation function EVA leads the user to another function menu, e.g. a menu as described with respect to FIG. 3. The user can now select at least one of the operation functions 47 according to step S4. Selection of an operation function 47 likewise comprises sending an activation request from the interface unit 20 to the evaluation unit 32.

In a step S5 evaluation unit 32 performs the selected evaluation function EVA/operation function 47 and thereby generates a result RES. By performing the evaluation function EVA/operation function 47, the evaluation unit 32 accounts for image data within the region of interest. With other words, the generated evaluation result RES is either based on image data entries of the displayed image data set MEDI, particularly the ones within the region of interest ROI or refers to at least one image element within the region of interest ROI, e.g. when the evaluation function comprises acquiring additional image data to be compared to the region of interest ROI. Step S5 may comprise sending the evaluation result RES to the visualization unit 33. The result RES may comprise evaluation data and/or additional data wherein evaluation data are based on image data within the region of interest and additional data are at least related to image data within the region of interest ROI and retrieved e.g. from storage unit 35. The evaluation result RES may correspond, but is not limited to one of the following types of evaluation results reference medical image data of a prior study covering the region of interest ROI,
prognosis medical image data indicative of a disease progression the prognosis relating to the region of interest,
a video of image data within the region of interest ROI,
a three-dimensional view of image data within the region of interest,
a magnified view of image data within the region of interest,
an augmented view of image data within the region of interest.

In a step S6 the visualization unit 33 generates a visualization of the evaluation result RES and displays is via output unit 21 to the user. Preferably, the result RES visualized as an overlay to the evaluation tool 40, most preferably it is visualized with in the field of view 44. Visualization unit 33 translates or converts calculates an evaluation result value into a suitable representation for displaying to the user. The suitable representation can be in the form of adapted image element entries for the region of interest or a projection plane to be superimposed to the displayed medical image data set comprising additional information. The suitable representation may further comprise visual rendering of evaluation result windows containing additional data to be displayed as an overlay to any image area of the displayed image data set MEDI. Accordingly, visualization unit 33 may be configured to run or execute an algorithm for creating an overlay image/window to be superimposed over the medical image data set MEDI. Visualization unit 33 may be configured to imply known volumetric rendering procedures, such as volume ray casting, splatting, shear wrapping or texture mapping.

Embodiments of the present invention are particularly advantageous in an oncological application. Here, the evaluation unit 32 may apply a model-based algorithm to predict disease progression or tumor growth with or without treatment based on at least some image element entries comprised in the region of interest. With other words, in this use case, one evaluation function may comprise applying a model or predictive algorithm to image element entries belonging to a identified lesion or tumor to predict its structural development. The algorithm may further include additional data like patient specific data, e.g. age, gender, genetic information or the like, which may be requested from storage unit 35.

As a result RES of the thus described evaluation function EVA, an image sequence might be displayed to the user, which visualizes lesion growth over time as a video clip. Alternatively or in addition, the user might scroll through the image series to inspect in detail individual images of the series. Thus, the present invention allows to derive profoundly recommendations for follow-up examinations and/ or to identify treatment options (by further visualizing potential treatment impact on the lesion).

In summary, embodiments of the invention relate to a method and system for image visualization and exploration which may comprise multiple components which interact to provide an easy-to use, fast and intuitive tool for detection and evaluation of suspicious image areas. An inventive interface unit of at least one embodiment allows the user to view a current imaging volume and navigate therein (eg. By scrolling, 3D rotation, navigate through time or the like). The interface unit may preferably be embodied as part of any PACS review/reading station.

An inventive evaluation tool 40 of at least one embodiment, together with corresponding subunits of at least one embodiment of the inventive computing unit 30 (most preferably embodied as a circular tool) allows inspection of any image area with/without requiring previous labeling of the image. The evaluation tool 40 allows to quickly explore relevant supplementary information on top/next to the image area (ROI) where the evaluation tool is applied.

At least one embodiment of the invention particularly addresses an optimized user interface to allow quick selection/browsing of different supplementary sources of information within one specific imaging context. Evaluation results, especially in the form of additional data may be visualized as a colorized overlay on top of the selected image area (ROI), e.g. a rotating 3D view, animated lesion growth over multiple examinations, different contrast, textual labels, extended tooltips, views showing visual or textural information next to and/or on top of the ROI. Deactivation of the evaluation tool 40 may immediately hide the tool itself and all its evaluation results RES and thus provide a clear view on the medical image data set MEDI as classically displayed.

Optionally, an inventive abnormality detection (unit 36) of at least one embodiment may include or apply at least one CAD algorithm to automatically detect areas of abnormality in the medical image data set MEDI, The abnormality detection may comprise a query sent to at least one database/storage unit 35 for retrieving previously reported findings with their anatomical position. The inventive abnormality detection of at least one embodiment may further display/visually indicate potential or known abnormalities and thus grab the user's attention directly within the displayed medical image data set MEDI at the relevant position/region. Abnormality indication may comprise overlay/labeling techniques or by applying temporary motion fields to the displayed abnormality, which by evolutionary nature humans are very sensitive to.

At least one embodiment of the invention could provide an essential improvement for a reading frontend by providing advanced data/information support for the decision-making radiologist. The inventive core of at least one embodiment lies in presenting a visual rendering of an evaluation tool comprising a plurality of evaluation functions to assist the user in generating medical findings and simplifying making diagnostic decisions.

Wherever meaningful, individual embodiments or their individual aspects and features can be combined or exchanged with one another without limiting or widening the scope of the present invention. Advantages which are described with respect to one embodiment of the present invention are, wherever applicable, also advantageous to other embodiments of the present invention.

The patent claims of the application are formulation proposals without prejudice for obtaining more extensive patent protection. The applicant reserves the right to claim even further combinations of features previously disclosed only in the description and/or drawings.

References back that are used in dependent claims indicate the further embodiment of the subject matter of the main claim by way of the features of the respective dependent claim; they should not be understood as dispensing with obtaining independent protection of the subject matter for the combinations of features in the referred-back dependent claims. Furthermore, with regard to interpreting the claims, where a feature is concretized in more specific detail in a subordinate claim, it should be assumed that such a restriction is not present in the respective preceding claims.

Since the subject matter of the dependent claims in relation to the prior art on the priority date may form separate and independent inventions, the applicant reserves the right to make them the subject matter of independent claims or divisional declarations. They may furthermore also contain independent inventions which have a configuration that is independent of the subject matters of the preceding dependent claims.

None of the elements recited in the claims are intended to be a means-plus-function element within the meaning of 35 U.S.C. § 112(f) unless an element is expressly recited using the phrase "means for" or, in the case of a method claim, using the phrases "operation for" or "step for."

Example embodiments being thus described, it will be obvious that the same may be varied in many ways. Such variations are not to be regarded as a departure from the spirit and scope of the present invention, and all such modifications as would be obvious to one skilled in the art are intended to be included within the scope of the following claims.

What is claimed is:

1. A system for supporting evaluation of a medical image data set, the system comprising
    an interface circuit configured to provide a display of a medical image data set to a user, visualize an evaluation tool, the evaluation tool being adapted to be movably arranged over the medical image data set displayed, and to provide at least two evaluation functions with respect to the medical image data set displayed, visualize at least one result of an evaluation function receive user input relating to navigating the evaluation tool in the medical image data set to a region of interest, and selecting at least one evaluation function of the at least two evaluation functions, and
    a processor configured to process the user input to navigate the evaluation tool in the medical image data set to the region of interest,
    perform the at least one evaluation function selected according to user input, wherein the performing of the at least one evaluation function selected including accounting for image data within the region of interest, and
    generate a visualization of at least one result of the at least one evaluation function selected,
    wherein the at least one result is adapted to be visualized as at least one of an overlay of the medical image data set displayed and an evaluation tool,
    wherein the interface circuit is further adapted to display the evaluation tool as a circular evaluation tool positioned as an overlay to the region of interest, and
    wherein the circular evaluation tool includes, at a center of the circular evaluation tool, a transparent circular field of view adapted to cover the region of interest and at a circumference of the circular evaluation tool, a rotatable ring subdivided into a plurality of ring segments, wherein each ring segment, of the plurality of ring segments, embodies an evaluation function activatable by rotating the rotatable ring such that a ring segment corresponding to at least one evaluation function selected, takes an activation position.

2. The system of claim 1, wherein at least one ring segment is further configured to, upon activation, generate an interactive operation menu comprising a plurality of evaluation operations related to the at least one evaluation function selected.

3. The system of claim 1, wherein the processor is further configured to detect at least one abnormality in the medical image data set.

4. The system of claim 3, wherein the interface circuit is further adapted to highlight the at least one abnormality detected.

5. The system of claim 4, wherein the interface circuit is configured to automatically position the evaluation tool as an overlay to the at least one abnormality highlighted.

6. The system of claim 1, wherein performing of the at least one evaluation function includes generating as a result of at least one of evaluation data and additional data, wherein the evaluation data are based on image data within the region of interest and the additional data are at least related to image data within the region of interest and retrieved from a data source.

7. The system of claim 6, wherein the processor is further configured to at least partially register image data within the region of interest with the at least one of the evaluation and the additional data.

8. The system of claim 7, wherein the at least one of the evaluation and the additional data include at least one of:
- reference medical image data of a prior study covering the region of interest, and
- prognosis medical image data indicative of a disease progression the prognosis relating to the region of interest.

9. The system of claim 7, wherein the at least one of the evaluation and the additional data include at least one of:
- a video of image data within the region of interest,
- a three-dimensional view of image data within the region of interest,
- a magnified view of image data within the region of interest, and
- an augmented view of image data within the region of interest.

10. The system of claim 6, wherein the at least one of the evaluation and the additional data include at least one of:
- reference medical image data of a prior study covering the region of interest, and
- prognosis medical image data indicative of a disease progression the prognosis relating to the region of interest.

11. The system of claim 6, wherein the at least one of the evaluation and the additional data include at least one of:
- a video of image data within the region of interest,
- a three-dimensional view of image data within the region of interest,
- a magnified view of image data within the region of interest, and
- an augmented view of image data within the region of interest.

12. A computer-implemented method for supporting evaluation of a medical image data set, the method comprising:
- providing a display of a medical image data set to a user,
- visualizing an evaluation tool adapted
  - to be movably arranged over the medical image data set displayed, and
  - to provide at least two evaluation functions with respect to the medical image data set displayed,
- receiving user input relating to navigating the evaluation tool in the medical image data set to a region of interest and relating to selecting at least one evaluation function, of the at least two evaluation functions, processing the user input to
  - navigate the evaluation tool in the medical image data set to the region of interest, and
  - perform the at least one evaluation function selected according to user input, wherein performing of the at least one evaluation function selected includes accounting for image data within the region of interest,
- generating a visualization of at least one result of the at least one evaluation function selected, and
- visualizing the at least one result of the at least one evaluation function selected,
- wherein the at least one result is visualized as at least one of an overlay to the medical image data set displayed and an evaluation tool,
- wherein the evaluation tool is displayed as a circular evaluation tool positioned as an overlay to the region of interest,
- wherein the circular evaluation tool includes, at a center of the circular evaluation tool, a transparent circular field of view adapted to cover the region of interest and at a circumference of the circular evaluation tool, a rotatable ring subdivided into a plurality of ring segments, and
- wherein each ring segment, of the plurality of ring segments, embodies an evaluation function activatable by rotating the rotatable ring such that a ring segment corresponding to at least one evaluation function selected, takes an activation position.

13. A non-transitory computer program product storing program elements to induce a processor of a system, for supporting evaluation of a medical image data set, to perform the method of claim 12, when the program elements are loaded into a memory of the processor and executed by the processor.

14. A non-transitory computer-readable medium storing program elements, readable and executable by a processor of a system for supporting evaluation of a medical image data set, to perform the method of claim 12, when the program elements are executed by the processor.

* * * * *